United States Patent [19]

Karjalainen et al.

[11] 4,333,947
[45] Jun. 8, 1982

[54] SUBSTITUTED IMIDAZOLES AND THEIR USE

[75] Inventors: Arto J. Karjalainen; Kauko O. A. Kurkela, both of Oulu, Finland

[73] Assignee: Farmos-Yhtyma Oy, Turku, Finland

[21] Appl. No.: 233,305

[22] Filed: Feb. 11, 1981

[30] Foreign Application Priority Data

Feb. 13, 1980 [GB] United Kingdom ............... 8004748

[51] Int. Cl.³ ........................................... C07C 233/96
[52] U.S. Cl. ............................... 424/273 R; 542/400; 542/457; 542/458; 542/468
[58] Field of Search ............... 542/468, 457, 458, 400; 424/273 R

[56] References Cited

U.S. PATENT DOCUMENTS

| 3,050,520 | 8/1962 | Erner et al. | 542/458 |
| 3,502,661 | 3/1970 | Kasubick et al. | 542/458 |
| 3,812,111 | 5/1974 | Wehrmeister | 542/458 |
| 3,991,201 | 11/1976 | Heeres et al. | 542/400 |
| 4,238,497 | 12/1980 | Black et al. | 424/273 R |
| 4,273,783 | 6/1981 | Diethelm | 424/273 R |

Primary Examiner—Arthur P. Demers

Attorney, Agent, or Firm—Armstrong, Nikaido, Marmelstein & Kubovcik

[57] ABSTRACT

The invention provides compounds of the formula:

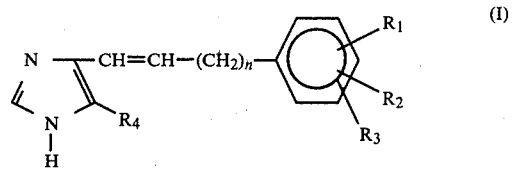

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or alkyl of 1 to 7 carbon atoms; and n is 0–3; and their non-toxic pharmaceutically acceptable acid addition salts. These compounds exhibit valuable pharmacological activity and are useful in the treatment of mammals, e.g. as anti-hypertensive, β-blocking and anti-thrombotic agents. Furthermore the compounds have remarkable antimicrobial activity. The compounds may be made by a variety of methods and may be incorporated in pharmaceutical compositions also comprising a compatible pharmaceutically acceptable carrier.

23 Claims, No Drawings

SUBSTITUTED IMIDAZOLES AND THEIR USE

DESCRIPTION

The present invention relates to substituted imidazole derivatives and their non-toxic, pharmaceutically acceptable acid addition salts, and their preparation, to pharmaceutical compositions containing the same, and to their use.

The imidazole derivatives of the present invention have the general formula:

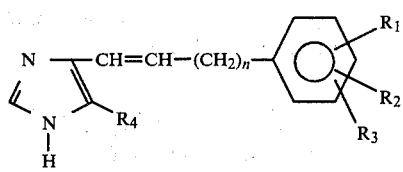

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; and n is an integer from 0–3.

The non-toxic pharmaceutically acceptable acid addition salts of these compounds are also within the scope of the invention.

The compounds of the formula (I) form acid addition salts with both organic and inorganic acids. They can thus form many pharmaceutically usable acid addition salts, such as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least one of the compounds of formula (I) or a non-toxic, pharmaceutically acceptable acid addition salt thereof, and a compatible pharmaceutically acceptable carrier therefor.

The present invention provides, for example, the following specific compounds of formula (I):
4-[3-(2',6'-dimethylphenyl)-1-propenyl]-imidazole
4-[2-(2',3'-dimethylphenyl)-ethenyl]-imidazole
4-[2-(2',6'-dimethylphenyl)-ethenyl]-imidazole
4-[5-(2',6'-dimethylphenyl)-1-pentenyl]-imidazole
4-[2-(2',6'-dichlorophenyl)-ethenyl]-imidazole
4-[3-(2',4'-dimethylphenyl)-1-propenyl]-imidazole
4-[3-(2',3'-dimethylphenyl)-1-propenyl]-imidazole
4-(3-phenyl-1-propenyl)-imidazole
4-[3-(2'-methylphenyl)-1-propenyl]-imidazole
4-[3-(3'-methylphenyl)-1-propenyl]-imidazole
4-[3-(4'-methylphenyl-1-propenyl]-imidazole
4-[3-(2',4',6'-trimethylphenyl)-1-propenyl]-imidazole
4-[3-(4'-ethylphenyl)-1-propenyl]-imidazole
4-[2-(3',4'-dihydroxyphenyl)-ethenyl]-imidazole
4-[5-(2'-methylphenyl)-1-pentenyl]-imidazole
4-[4-(2',6'-dichlorophenyl)-1-butenyl]-imidazole
4-[2-(2',6'-dichlorophenyl)-ethenyl]-5-methyl-imidazole
4-[2-(2'-chlorophenyl)-ethenyl]-5-methyl-imidazole
4-[3-(3'-methoxyphenyl)-1-propenyl]-imidazole
4-[2-(2',6'-dimethylphenyl)-ethenyl]-5-methyl-imidazole
4-[2-(2',4',6'-trimethylphenyl)-ethenyl]-imidazole
4-[2-(2',3'-dichlorophenyl)-ethenyl]-imidazole
4-[2-(2',3'-dimethylphenyl)-ethenyl]-5-methyl-imidazole
4-[2-(2',6'-diethylphenyl)-ethenyl]-imidazole
4-[2-(2',3'-diethylphenyl)-ethenyl]-imidazole
4-[2-(2',6'-dimethoxyphenyl)-ethenyl]-imidazole
4-[2-(2',6'-difluorophenyl)-ethenyl]-imidazole
4-[2-(2',6'-dibromophenyl)-ethenyl]-imidazole
4-[3-(2',6'-dimethylphenyl)-1-propenyl]-5-methyl-imidazole
4-[3-(2',6'-diethylphenyl)-1-propenyl]-imidazole
4-[3-(2'-bromophenyl)-1-propenyl]-imidazole
4-[3-(3'-chlorophenyl)-1-propenyl]-imidazole
4-[3-(4'-chlorophenyl)-1-propenyl]-5-methyl-imidazole
4-[3-(2',6'-dichlorophenyl)-1-propenyl]-imidazole
4-[3-(2',6'-dibromophenyl)-1-propenyl]-imidazole
4-(4-phenyl-1-butenyl)-5-methyl-imidazole
4-[3-(2',3'-difluorophenyl)-1-propenyl]-imidazole
4-[3-(2',3'-dimethoxyphenyl)-1-propenyl]-imidazole
4-[3-(2',4'-dihydroxyphenyl)-1-propenyl]-imidazole
4-[3-(2'-hydroxyphenyl)-1-propenyl]-imidazole
4-[4-(2',4'-dichlorophenyl)-1-butenyl]-imidazole
4-[4-(2',6'-dimethoxyphenyl)-1-butenyl]-imidazole
4-[4-(2',3'-diethylphenyl)-1-butenyl]-imidazole
4-[4-(2',6'-dimethylphenyl)-1-butenyl]-imidazole
4-4-(2'-hydroxyphenyl)-1-butenyl]-imidazole
4-[5-(2'-bromophenyl)-1-pentenyl]-imidazole
4-[5-(2',6'-dichlorophenyl)-1-pentenyl]-imidazole
4-[5-(3'-methoxyphenyl)-1-pentenyl]-imidazole
4-[5-(2',6'-dimethylphenyl)-1-pentenyl]-5-methyl-imidazole
4-[3-(2',3'-dimethylphenyl)-1-propenyl]-5-methyl-imidazole
4-(3-phenyl-1-propenyl)-5-methyl-imidazole
4-(2-phenylethenyl)-5-methyl-imidazole
4-[3-(4'-methylphenyl)-1-propenyl]-5-methyl-imidazole
4-[3-(3'-methylphenyl)-1-propenyl]-5-methyl-imidazole
4-[2-(3',4'-dimethylphenyl)-ethenyl]-5-methyl-imidazole
4-[2-(2',5'-dimethylphenyl)-ethenyl]-5-methyl-imidazole The compounds of the present invention have been found to possess good antihypertensive properties. Preliminary tests have shown that they also possess other valuable pharmacological properties, for example, β-blocking, antithrombotic and diuretic activity. Furthermore the compounds have proved to possess remarkable antimicrobial activity.

While all of the compounds of formula (I) have the aforementioned activities, certain groups of the compounds remain preferred. One such preferred group can be represented by the structural formula:

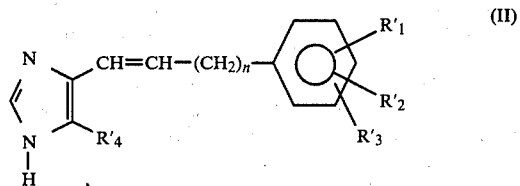

wherein n is the same as before; each of $R'_1$, $R'_2$ and $R'_3$ is hydrogen, chloro, methyl, ethyl, methoxy or hydroxy; and $R'_4$ is hydrogen or methyl.

According to a feature of the invention, the compounds of formula (I) are prepared by dehydration of the corresponding imidazoles of the formula:

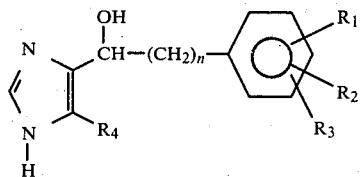

wherein $R_1$, $R_2$, $R_3$ and $R_4$ are defined as before and n is 1–4. The dehydration is carried out according to known methods for instance by refluxing the hydroxysubstituted compound in an appropriate acidic solution, e.g. concentrated hydrochloric acid. Alternatively the hydroxy-substituted imidazole can be dehydrated by heating it together with anhydrous potassium hydrogen sulfate.

The compounds of formula (III) are made by a Grignard reaction in which an imidazole aldehyde of the formula:

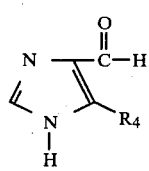

wherein $R_4$ is defined as before, is reacted with an arylalkyl magnesium halide derivative of the formula:

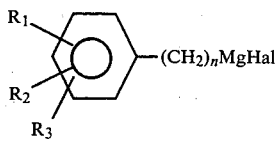

wherein $R_1$, $R_2$, and $R_3$ are defined as before, n is an integer from 1–4 and Hal is a halogen atom.

The arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofuran. The arylalkylmagnesiumhalide derivative is prepared in the usual way by adding the arylalkylmagnesiumhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4-imidazole derivative is added in solid form in small portions. After the addition, the reaction mixture is refluxed until all of the 4-imidazole derivative has reacted.

The reaction time varies between one and five hours. In the reaction, at least two equivalents of arylalkylmagnesiumhalide are used per one equivalent of 4-imidazolealdehyde, because the last mentioned compound contains active hydrogen which binds a part of the Grignard reagent.

The above described Grignard reaction utilizing a 4-imidazolealdehyde as starting material is a surprising and new method for the synthesis of imidazole derivatives. The process is surprising in view of the teachings of the prior art. Thus, for example, Deulofeu et al., *J.Org.Chem.*, 14, 1949, 915 states that 4-imidazolealdehyde does not react with methylmagnesiumiodide, i.e., in the Grignard reaction.

Another process for the preparation of compounds of formula (I) is a Wittig reaction which comprises reacting an imidazole aldehyde of the formula:

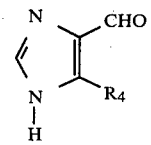

wherein $R_4$ is the same as before, with an aralkylidenetriphenylphosphorane of the formula:

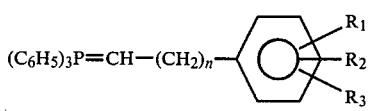

wherein $R_1$, $R_2$ and $R_3$ are the same as before and n is 0–3. The aralkylidenetriphenylphosphoranes are preferably prepared by reacting the corresponding aralkyltriphenylphosphonium halide of the formula:

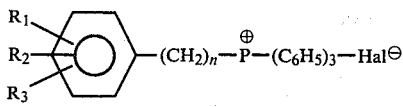

wherein $R_1$, $R_2$ and $R_3$ are the same as before, n is 0–4 and Hal is a halogen atom, with a basic reagent, preferably butyllithium.

The processes described above for the preparation of compounds of formula (I) result mainly in the trans isomer of the compound. The trans isomer can be converted to the cis isomer according to known methods, e.g. by heating it in the presence of an acid or by irradiating it with ultraviolet light.

Yet another process for the preparation of the compounds of formula (I), wherein $R_4$ is hydrogen or methyl, comprises reacting a compound of the formula:

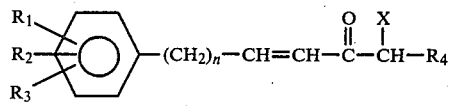

wherein $R_1$, $R_2$ and $R_3$ are defined as before, X is a halogen atom or hydroxy, $R_4$ is hydrogen or methyl and n is 0–3 with a reagent capable of converting said starting material to the corresponding imidazole of the formula:

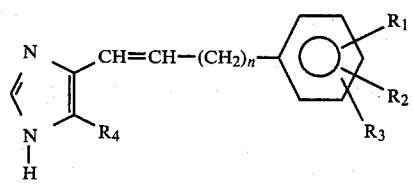

Formamide is preferably used as the reagent.

As stated herein above, the compounds of the general formula (I) and their non-toxic, pharmaceutically acceptable acid addition salts have valuable pharmacological properties and have been found to possess good anti-hypertensive activity in mammals. This activity makes these imidazole derivatives particularly useful in the treatment of high blood pressure. Furthermore the compounds have proved to possess remarkable antimicrobial activity. Preliminary tests have shown that they also possess other pharmacological properties, for example, $\beta$-blocking, antithrombotic and diuretic activity.

Administration of isomeric compounds of formula (I), their non-toxic, pharmaceutically acceptable acid salts or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The anti-hypertensive properties of the imidazole derivatives of the present invention have been determined according to the following procedure. Sprague-Dawley rats of normal weight were first anesthetized with urethane. After this, the femoral artery was connected by way of a polyethylene tube with a blood pressure transducer. The test substance was then injected into the femoral vein and the blood pressure and the pulse frequency were registered with a recorder.

The antimicrobial activity was determined in vitro according to a qualitative test for antibacterial and antifungal activity, using the agar diffusion method, against the following standard organisms: *Staphylococcus aureus, Streptococcus pyogenes, Escherichia coli, Proteus mirabilis, Pseudomonas aeruginosus, Candida albicans* and *Aspergillus niger*.

The $\beta$-blocking activity was measured in vitro as follows: The atrium of a guinea-pig was isolated. The inhibiting activity of the compound against isoprenaline-induced chronotropic and inotropic action in the isolated atrium was measured.

The antithrombotic activity was investigated in vivo in mice as follows: The compounds to be tested were administered orally. After this arachidonic acid was given i.v. The inhibiting activity of the test compounds against arachidonic acid induced pulmonary thromboembolism was investigated.

In a further test the antithrombotic activity was investigated in vitro. The inhibiting activity of the compounds against ADP- and collagen-induced aggregation of thrombocytes was measured. In the test thrombocytes from a cow was used. To 1.2 ml of plasma containing 250000 thrombocytes/mm$^3$ were added 50 $\mu$l of a solution of the compound to be tested. After 10 min incubation either ADP or collagen was added. The aggregation of the thrombocytes was turbidimetrically determined at $\lambda = 605$ n m.

Acute toxicity was determined by using female mice of NMRI-Strain with an age of about 7 months and weighing 30–40 g. The administration of the test compound was i.v.

Thus, the trans isomer of the compound 4-[2-(2',6'-dimethylphenyl)-ethenyl]-imidazole, which has a LD$_{50}$ value of 50 mg/kg i.v. in mice was found in the blood pressure study with anesthetized rats of normal weight described above to cause a registrable lowering of the blood pressure with a dose of 10 $\mu$g/kg i.v. With a dose of 300 $\mu$g/kg i.v., the reduction of the blood pressure was 20%, and the decrease of pulse frequency was 24%. The effect was measured 20 minutes after administration.

For the compound 4-[2-(2',6'-dichlorophenyl)-ethenyl]-5-methyl-imidazole having a LD$_{50}$ of 100 mg/kg i.v. in mice, a registrable lowering of the blood pressure was measured with a dose of 300 $\mu$g/kg i.v., and a decrease of pulse frequency was noticed at a dose of 1 mg/kg i.v.

A dose of 3 mg/kg i.v. caused 30% lowering of the blood pressure measured 20 minutes after administration.

For the compound 4-[3-(2',6'-dimethylphenyl)-1-propenyl]-imidazole having a LD$_{50}$ of 75 mg/kg i.v. in mice, a dose of 1–3 mg/kg i.v. gave a 20% decrease of the blood pressure measured 20 minutes after administration.

For the compound 4-[3-(2',3'-dimethylphenyl)-1-propenyl]-imidazole having a LD$_{50}$ of 75 mg/kg i.v. in mice, a dose of 0.3–1 mg/kg i.v. caused a 20% decrease of the blood pressure measured 20 minutes after administration.

For the compound 4-[2-(2',6'-dichlorophenyl)-ethenyl]-imidazole having a LD$_{50}$ of 85 mg/kg i.v. in mice the lowering of the blood pressure was 25% with a dose of 1 mg/kg i.v. With the same dose, the pulse frequency decreased with 30%. The registration was performed 20 minutes after administration.

In the antimicrobial test the compound 4-[2-(2',6'-dichlorophenyl)-ethenyl]-imidazole was active at 1000 $\mu$g/ml against all standard bacterial and fungal species.

The compound 4-[2-(2'-chlorophenyl)-ethenyl]-5-methyl-imidazole having a LD$_{50}$ of 85 mg/kg i.v. in mice was active at 1000 $\mu$g/ml against all the bacterial species, but not against the fungi.

The compound 4-[2-(2',6'-dichlorophenyl)-ethenyl]-5-methyl-imidazole was active at 1000 $\mu$g/ml against all the bacterial species and *Candida albicans*, but was inactive against *Aspergillus niger*.

The compound 4-[5-(2',6'-dimethylphenyl)-1-pentenyl]-imidazole having a LD$_{50}$ of 40 mg/kg i.v. in mice was active at 100 $\mu$g/ml against *E. coli* and *Staph. aureus*. At 1000 $\mu$g/ml it was active against all other bacterial and fungal species.

In the $\beta$-blocking activity test, the compound 4-[2-(2'-chlorophenyl)-ethenyl]-5-methyl-imidazole gave at a concentration of 1 $\mu$g/ml a 67 percent inhibition of isoprenaline-induced chronotropic effect.

The compound 4-[5-(2',6'-dimethylphenyl)-1-pentenyl]-imidazole caused a 57 percent inhibition of isoprenaline induced chronotropic effect at a concentration of 1 $\mu$g/ml.

In the antithrombotic activity test (in vivo), the compound 4-[2-(2'-chlorophenyl)ethenyl]-5-methylimidazole protected 4 of 5 mice from arachidonic acid-induced pulmonary thromboembolism at a dose of 10 mg/kg p.o.

According to the in vitro test for antithrombotic activity the compound 4-[3-(2',3'-dimethylphenyl)-1-propenyl]-imidazole inhibited the collagen-induced thrombocyte aggregation completely and the ADP-induced aggregation clearly. $LD_{50} = 75$ mg/kg in mice.

The compound 4-[2-(2',6'-dichlorophenyl)-ethenyl]-imidazole gave the following diuretic effect:

| Dosage, mg/kg | diuretic effect, % (5h) |
| --- | --- |
| 0.005 | 128 |
| 0.05 | 132 |
| 0.5 | 135 |

The diuretic effect was studied in rats by collecting the urine output during 0-5 hours after i.p. injection of the compound. Before the test the rats were fasting overnight and got 10 ml water p.o. immediately before the injection.

In the Examples below, where $1_H$-NMR or $13_C$-NMR spectrum shifts are presented, the NMR spectra were determined with a Brucker WB 80 DS apparatus using tetramethylsilane or 3-(trimethylsilyl)-propansulfonacid sodium salt standard, from which the presented chemical shifts ($\delta$,ppm) are tabulated. The letters s, d, t and m are used to indicate a singlet, doublet, triplet or multiplet, respectively. In the same connection, the number of hydrogen atoms is also stated. In some of the examples the coupling constants J ($H_z$) are given for protons typical for trans and cis isomers. The compounds which are indicated as bases are tested in deuterium methanol, deuterium acetone or deuterium chloroform, while the values for compounds which are indicated as hydrochlorides were determined in deuterium oxide.

The mass-spectra were determined with a Perkin-Elmer RMU apparatus using direct inlet system. The temperature employed was the lowest temperature needed for the evaporation of the compound as base. In the examples the strongest and the most essential fragment-ions from a structural viewpoint are given as m/e values. In parenthesis is given the intensity of the fragment-ion in relation to the main peak.

The following Examples illustrate the invention, in which the products principally occur as trans isomers (if there is no mention about isomer relationships).

EXAMPLE 1

4-[3-(2',6'-Dimethylphenyl)-1-hydroxypropyl]-imidazole 4.8 g of dry magnesium turnings are covered with 100 ml of dry tetrahydrofuran (THF). The mixture is heated to boiling and a solution of 42.6 g of 2-(2',6'-dimethylphenyl)-1-bromoethane in 100 ml of dry tetrahydrofuran is added dropwise at such a rate that gentle refluxing is maintained. After the addition is complete, the reaction mixture is refluxed for an additional 30 minutes.

The reaction mixture is cooled to 50° C. and 7.0 g of 4-imidazolealdehyde is added slowly in small portions. After the addition is complete, the mixture is refluxed for 5 hours. Then the reaction mixture is cooled and poured into 200 ml of cold water containing 20 ml of concentrated hydrochloric acid. Part of the tetrahydrofuran is distilled off to give a smaller volume and the tetrahydrofuran is replaced with water. The mixture is washed twice with 50 ml portions of chloroform. The aqueous layer is made alkaline with sodium hydroxide solution (pH about 8). The precipitate which forms is washed with water and added to 100 ml of 4 N NaOH solution and the mixture is stirred vigorously for one hour. The precipitate is filtered, washed several times with water and dried. The crude product is recrystallized from a mixture of water and ethanol to give 10.1 g of a product melting at 157°-158° C.

$^1$H-NMR: 2.3 (m, 2H), 2.6 (s, 6H), 3.0 (m, 2H), 5.15 (t, 1H), 5.45 (s, 2H), 7.25 (s, 3H), 7.35 (s, 1H), 8.0 (s, 1H).

MS: 230 (21%), 212 (20%), 197 (13%), 133 (11%), 124 (7%), 119 (18%), 118 (23%), 117 (18%), 115 (11%), 111 (98%) 98 (100%), 97 (69%), 95 (8%), 93 (7%), 91 (21%), 82 (27%), 81 (10%).

EXAMPLE 2

4-[3-(2',6'-Dimethylphenyl)-1-propenyl]-imidazole 10 g of 4-[3-(2',6-dimethylphenyl)-1-hydroxypropyl]-imidazole is refluxed in 100 ml of concentrated hydrochloric acid for 10 hours. After cooling, the solution is extracted with chloroform. The combined chloroform extracts are washed with 10 percent sodium hydroxide solution, then with water, dried and evaporated to dryness. The residue which is crude product is purified further by column chromatography using a Merck's reversed phase column, eluting the column with methanol. The melting point of the product is 162°-168° C. (as hydrochloride from ethyl acetate).

$^1$H-NMR (HCl-salt): trans isomer: 2.0 (s, 6H), 3.2 (d, 2H), 4.7 (s, 2H), 5.7 (d, 1H J: 16.5 $H_z$, typical for trans isomer), 6.05 (m, 1H), 6.6 (s, 1H), 6.7 (s, 3H), 8.4 (s, 1H)

EXAMPLE 3

4-[2-(2',6'-Dichlorophenyl)-ethenyl]-imidazole 6.5 g of 4-[2-(2',6'-Dichlorophenyl)-1-hydroxyethyl]-imidazole is mixed with 25 g of anhydrous potassium hydrogen sulfate and the mixture is warmed on oil bath at 150°-155° C. for 3 hours. The mixture is then cooled and 30 ml of methanol are added. The mixture is stirred and filtered. The cake is washed with methanol, the methanol filtrates are combined and evaporated to dryness. The residue is dissolved in methylene chloride, which is washed first with a dilute sodium hydroxide solution and then with water. Then it is evaporated to dryness. The residue is dissolved in isopropanol and the pH is adjusted to 4 with HCl-ethylacetate. The hydrochloride of the product is filtered and washed with ethylacetate. The hydrochloride salt melts at 207°-212° C. The free base is liberated from the hydrochloride in water with sodium hydroxide. The melting point of the base is 156°-157° C.

EXAMPLE 4

4-[2-(2',3'-Dimethylphenyl)-ethenyl]-imidazole 51.5 g of 2,3-dimethylbenzyl-triphenylphosphonium chloride is dissolved in 300 ml of tetrahydrofuran. The mixture is warmed to 40° C. Then 78 ml of a hexane solution of butyl lithium (butyl lithium concentration 1,66 mol/l) are added in a nitrogen atmosphere during 1-2 hours at such a rate that a temperature of 40°-50° C. is maintained with gentle cooling. After the addition is complete, the mixture is stirred at about 60° C. for another 2 hours. The reaction mixture is then cooled to 20° C. after which 9.6 g of 4-imidazolealdehyde is added in small portions. The mixture is stirred at 60° C. for 5 hours. The reaction mixture is then cooled to about 20° C. and 300 ml of water is added. Then the mixture is evaporated to a smaller volume, after which water is added again to replace the evaporated solvents. The pH is adjusted to 3–4 with HCl and the mixture is washed with toluene. The aqeuous layer is made alkaline, and the precipitate, which contains the crude product, is removed by filtration, washed and dried. The product is converted into the hydrochloride in toluene by adding HCl-ethylacetate. The hydrochloride, after recrystallization from water, melts at 204°–207° C. The base, which is liberated from the hydrochloride in water, has a melting point of 179°–183° C.

$^1$H-NMR (trans isomer): 2.3 (s, 6H), 3.75 (s, 1H), 6.8 (d, 1H. J: 16.1 H$_z$, typical for trans isomer), 7.0–7.57 (m, 6H).

EXAMPLE 5

4-[2-(2',6'-Dimethylphenyl)-ethenyl]-imidazole

The procedure of example 4 is repeated, except that 2,6-dimethylbenzyltriphenylphosphonium chloride is used as starting material in place of 2,3-dimethylbenzyltriphenylphosphonium chloride. Almost pure trans isomer is obtained as reaction product. This is convertend to the hydrochloride in ethylacetate by adding HCl-ethylacetate. The melting point of the hydrochloride is 208°–215° C. The base, which is liberated from the hydrochloride in water with sodium hyroxide, has a melting point of 123°–130° C.

The trans isomer is converted to the cis isomer by irradiating the former with ultraviolet light for 2 days in toluene solution. This results in a mixture containing about 30% of the trans isomer and about 70% of the cis isomer. The isomers are separated by liquid chromatography, eluating with a mixture of methanol and chloroform. The trans isomer (HCl-salt) has a melting point of 213°–217° C. The cis isomer (HCl-salt) melts at 237°–240° C.

$^1$H-NMR (trans isomer): 2.3 (s, 6H), 5.6 (s, 1H), 6.45 (d, 1H, J: 16.8 H$_z$, typical for trans isomer), 6.9–7.2 (m, 5H), 7.6 (s, 1H).

$^{13}$C-NMR (trans isomer): 115.13 (d), 117.67 (d), 127.66 (d), 128.11 (d), 132.14 (d), 132.44 (s), 133.38 (d), 134.86 (s), 136.20 (s).

$^1$H-NMR (cis isomer): 2.2 (s, 6H), 6.3 (d, 1H. J: 11.8 H$_z$, typical for cis isomer), 6.4 (s, 1H), 6.6 (d, 1H. J: 11.8 H$_z$, typical for cis isomer), 7.1 (s, 3H), 7.3 (s, 1H), 9.8 (s, 1H).

$^{13}$C-NMR (cis isomer): 114.91 (d), 116.55 (d), 128.20 (d), 128.20 (d), 130.44 (s), 131.96 (d), 134.62 (d), 134.83 (s), 135.35 (s).

In the examples 6–14 the procedure of example 3 is repeated, except that in place of 4-[2-(2',6'-dichlorophenyl)-1-hydroxyethyl]-imidazole is used the corresponding 4-[(substituted phenyl)-1-hydroxyalkyl]-imidazole.

EXAMPLE 6

4-[5-(2',6'-Dimethylphenyl)-1-pentenyl]-imidazole

M.p. of the hydrochloride 172°–180° C.

EXAMPLE 7

4-[3-(2',4'-Dimethylphenyl)-1-propenyl]-imidazole

M.p. 158°–165° C. (from diisopropylether).

EXAMPLE 8

4-[3-(2',3'-Dimethylphenyl)-1-propenyl]-imidazole

M.p. of the hydrochloride 172°–182° C. (from isopropanol-ether).

EXAMPLE 9

4-(3-Phenyl-1-propenyl)-imidazole

M.p. of the hydrochloride 148°–153° C. (from isopropanol).

EXAMPLE 10

4-[3-(2'-Methylphenyl)-1-propenyl]-imidazole

M.p. of the hydrochloride 174°–178° C. (from isopropanol).

EXAMPLE 11

4-[3-(4'-Methylphenyl)-1-propenyl]-imidazole

M.p. of the hydrochloride 179°–184° C. (from isopropanol).

EXAMPLE 12

4-[3-(2',4',6'-Trimethylphenyl)-1-propenyl]-imidazole

M.p. of the base 74°–84° C.

EXAMPLE 13

4-[3-(4'-Ethylphenyl)-1-propenyl]-imidazole

M.p. of the base 70°–74° C.

EXAMPLE 14

4-[5-(2'-Methylphenyl)-1-pentenyl]-imidazole $^1$H-NMR (HCl-salt): 1.8 (m, 2H), 2.2 (s, 3H), 2.6 (m, 4H), 5.0 (s, 2H), 5.8-6.3 (m, 2H), 7.1 (m, 5H), 8.6 (s, 1H).

In the examples 15–22 the procedure of example 3 is repeated, except that in place of 4-[2-(2',6'-dichlorophenyl)-1-hydroxyethyl]-imidazole is used the corresponding 4-[(substituted phenyl)-1-hydroxyalkyl]-5-methyl-imidazole.

EXAMPLE 15

4-(3-phenyl-1-propenyl)-5-methyl-imidazole

M.p. of the hydrochloride 202°–205° C.

EXAMPLE 16

4-(2-phenylethenyl)-5-methyl-imidazole

M.p. of the hydrochloride 250° C.

EXAMPLE 17

4-[2-(2',3'-dimethylphenyl)-ethenyl]-5-methyl-imidazole

M.p. of the base 204°–206° C.

EXAMPLE 18

4-[2-(2',6'-Dichlorophenyl)-ethenyl]-5-methyl-imidazole

M.p. of the hydrochloride 104°–109° C. M.p. of the base 80°–86° C.

EXAMPLE 19

4-[2-(2'-Chlorophenyl)-ethenyl]-5-methyl-imidazole

M.p. of the hydrochloride 230°–234° C. (from isopropanol-ether).

EXAMPLE 20

4-[2-(2',5'-dimethylphenyl)-ethenyl]-5-methyl-imidazole

M.p. of the hydrochloride 204°–208° C.

EXAMPLE 21

4-[2-(3',4'-dimethylphenyl)-ethenyl]-5-methyl-imidazole

M.p. of the hydrochloride 214°–226° C. (the products include about 10% of the cis isomer).

EXAMPLE 22

4-[3-(4'-methylphenyl)-1-propenyl]-5-methyl-imidazole

M.p. of the hydrochloride 215°–216° C.

EXAMPLE 23

4-[3-(3'-Methoxyphenyl)-1-propenyl]-imidazole

The procedure of example 4 is repeated except that, 2-(3-methoxyphenyl)-ethyltriphenylphosphonium chloride is used in place of 2,3-dimethylbenzyltriphenylphosphonium chloride. M.p. of the hydrochloride 128°–132° C.

EXAMPLE 24

4-[2-(2',6'-dimethylphenyl)-ethenyl]-5-methyl-imidazole

The procedure of example 3 is repeated except that 4-[2-(2',6'-dimethylphenyl)-1-hydroxyethyl]-5-methyl-imidazole is used in place of 4-[2-(2',6'-dichlorophenyl)-1-hydroxyethyl]-imidazole.

M.p. of the hydrochloride 207°–210° C.

$^1$H-NMR: 2.415 (s, 6H), 2.441 (s, 3H), 5.03 (s, 2H), 6.51 (d, 1H), 7.14 (s, 3H), 7.24 (d, 1H), 8.78 (s, 1H)

We claim:

1. A substituted imidazole of the formula:

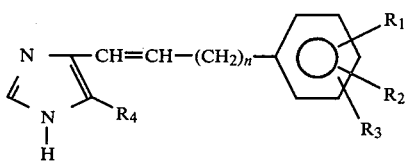

wherein each of $R_1$, $R_2$ and $R_3$, which can be the same or different, is hydrogen, chloro, bromo, fluoro, methyl, ethyl, methoxy, amino, hydroxy or nitro; $R_4$ is hydrogen or an alkyl radical of 1 to 7 carbon atoms; and n is an integer from 0–3, and its non-toxic pharmaceutically acceptable acid addition salts.

2. A compound according to claim 1, wherein each of $R_1$, $R_2$ and $R_3$, which can be the same or different, is hydrogen, chloro, methyl, ethyl, methoxy, or hydroxy.

3. A compound according to claim 1, wherein $R_1$ is hydrogen, chloro, methyl, ethyl or methoxy and each of $R_2$ and $R_3$, which can be the same or different, is chloro, methyl, ethyl or methoxy.

4. A compound according to claim 1, 2, or 3, wherein $R_4$ is hydrogen or methyl.

5. 4-[3-(2',6'-Dimethylphenyl)-1-propenyl]-imidazole and its non-toxic pharmaceutically acceptable acid addition salts.

6. 4-[2-(2',3'-Dimethylphenyl)-ethenyl]-imidazole and its non-toxic pharmaceutically acceptable acid addition salts.

7. 4-[2-(2',6'-Dimethylphenyl)-ethenyl]-imidazole and its non-toxic pharmaceutically acceptable acid addition salts.

8. 4-[5-(2',6'-Dimethylphenyl)-1-pentenyl]-imidazole and its non-toxic pharmaceutically acceptable acid addition salts.

9. 4-[2-(2',6'-Dichlorophenyl)-ethenyl]-imidazole and its non-toxic pharmaceutically acceptable acid addition salts.

10. 4-[3-(2',4'-Dimethylphenyl)-1-propenyl]-imidazole and its non-toxic pharmaceutically acceptable acid addition salts.

11. 4-[3-(2',3'-Dimethylphenyl)-1-propenyl]-imidazole and its non-toxic pharmaceutically acceptable acid addition salts.

12. 4-[2-(2',6'-Dichlorophenyl)-ethenyl]-5-methylimidazole and its non-toxic pharmaceutically acceptable acid addition salts.

13. 4-[2-(2'-Chlorophenyl)-ethenyl]-5-methylimidazole and its non-toxic pharmaceutically acceptable acid addition salts.

14. A pharmaceutical composition useful for treating hypertension comprising an anti-hypertensive effective amount of a substituted imidazole as claimed in claim 1 or a non-toxic pharmaceutically acceptable acid addition salt thereof in association with a compatible pharmaceutically acceptable carrier.

15. A pharmaceutical composition useful for killing microbes which comprises an anti-microbially effective amount of a substituted imidazole as claimed in claim 1 or a non-toxic pharmaceutically acceptable acid addition salt thereof in association with a compatible pharmaceutically acceptable carrier.

16. A pharmaceutical composition useful for treating thrombosis which comprises an anti-thrombotically effective amount of a substituted imidazole as claimed in claim 1 or a non-toxic pharmaceutically acceptable acid addition salt thereof in association with a compatible pharmaceutically acceptable carrier.

17. A pharmaceutical composition useful for blocking β-receptors in a subject in whom such block may be beneficial comprising an amount effective to block said β-receptors of a substituted imidazole as claimed in claim 1 or a non-toxic pharmaceutically acceptable acid addition salt thereof in association with a compatible pharmaceutically acceptable carrier.

18. A composition as claimed in claim 14, 15, 16, or 17, in which the carrier is a solid.

19. A composition as claimed in claim 14, 15, 16, or 17 in the form of a tablet, capsule, suppository, sterile solution, emulsion or powder.

20. Method of treating hypertension which comprises administering to a subject suffering therefrom or subject thereto an effective amount of a substituted imidazole as claimed in claim 1 or a non-toxic pharmaceutically acceptable acid addition salt thereof.

21. Method of killing microbes which comprises exposing said microbes to an effective toxic amount of a substituted imidazole as claimed in claim 1 or a non-toxic pharmaceutically acceptable acid addition salt thereof.

22. Method of treating thrombosis which comprises administering to a subject suffering therefrom or subject thereto an effective amount of a substituted imidazole as claimed in claim 1 or a non-toxic pharmaceutically acceptable acid addition salt thereof.

23. Method of blocking β-receptors in a subject in whom such block may be beneficial which comprises administering to such subject an effective amount of a substituted imidazole as claimed in claim 1 or a non-toxic pharmaceutically acceptable acid addition salt thereof.

* * * * *